US010646476B2

(12) United States Patent
Rumio et al.

(10) Patent No.: US 10,646,476 B2
(45) Date of Patent: May 12, 2020

(54) METHOD FOR TREATMENT OF HUMORAL SECRETION DYSFUNCTIONS

(71) Applicant: Metis Healthcare S.r.l., Milan (IT)

(72) Inventors: Cristiano Umberto Rumio, Milan (IT); Francesco Palladini, Milan (IT)

(73) Assignee: Metis Healthcare S.r.l., Milan (IT)

( * ) Notice: Subject to any disclaimer, the term of this patent is extended or adjusted under 35 U.S.C. 154(b) by 0 days.

(21) Appl. No.: 15/747,802

(22) PCT Filed: Jul. 26, 2016

(86) PCT No.: PCT/IB2016/054443
§ 371 (c)(1),
(2) Date: Jan. 26, 2018

(87) PCT Pub. No.: WO2017/021816
PCT Pub. Date: Feb. 9, 2017

(65) Prior Publication Data
US 2018/0207134 A1 Jul. 26, 2018

(30) Foreign Application Priority Data

Jul. 31, 2015 (IT) .................. 102015000041027

(51) Int. Cl.
| A61K 38/05 | (2006.01) |
| A61K 31/4172 | (2006.01) |
| A61K 9/00 | (2006.01) |
| A61K 9/06 | (2006.01) |
| A61K 9/20 | (2006.01) |
| A61K 35/20 | (2006.01) |
| A61K 36/185 | (2006.01) |
| A61K 36/48 | (2006.01) |
| A61K 47/12 | (2006.01) |

(52) U.S. Cl.
CPC .......... *A61K 31/4172* (2013.01); *A61K 9/006* (2013.01); *A61K 9/0034* (2013.01); *A61K 9/06* (2013.01); *A61K 9/20* (2013.01); *A61K 9/205* (2013.01); *A61K 9/2013* (2013.01); *A61K 9/2054* (2013.01); *A61K 35/20* (2013.01); *A61K 36/185* (2013.01); *A61K 36/48* (2013.01); *A61K 38/05* (2013.01); *A61K 47/12* (2013.01)

(58) Field of Classification Search
None
See application file for complete search history.

(56) References Cited

U.S. PATENT DOCUMENTS

| 5,238,931 A * | 8/1993 | Yoshikawa | .......... A61K 31/415 514/184 |
| 6,339,088 B1 * | 1/2002 | Ueno | .................. A61K 31/00 514/266.3 |
| 2002/0103244 A1 * | 8/2002 | Matahira | .............. A61K 31/415 514/396 |
| 2016/0206523 A1 * | 7/2016 | Obias | ....................... A61K 8/34 |

FOREIGN PATENT DOCUMENTS

| CN | 102100693 A * | 6/2011 |
| EP | 1210940 A2 | 6/2002 |
| WO | WO 2014/140890 A2 | 9/2014 |

OTHER PUBLICATIONS

Watanabe, T. et al. Polaprezinc Prevents Oral Mucositis Associated with Radiochemotherapy in Patients with Head and Neck Cancer. International J of Cancer 127:1984-1990, 2010. (Year: 2010).*
Baran E. Metal Complexes of Carnosine. Biochemistry (Moscow) 65(7)789-797, 2000. (Year: 2000).*
Macchi F. et al. Effects on Salivation on the Muco-Adhesive Dietary Supplement Aqualief in Xerostomic Patients. Supportive Care in Cancer 25(2)Suppl 1, S157 2017. (Year: 2017).*
T. Watanabe et al., "Polaprezinc prevents oral mucositis associated with radiochemotherapy in patients with head and neck cancer", International Journal of Cancer, vol. 127, No. 8, Oct. 15, 2010, pp. 1984-1990.
H. Hayashi et al., "Polaprezinc Prevents Oral Mucositis in Patients Treated with High-dose Chemotherapy Followed by Hematopoietic Stem Cell Transplantation", Anticancer Research Greece, vol. 34, No. 12, Dec. 1, 2014, pp. 7271-7278.
A. Pedersen et al., "Oral findings in patients with primary Sjogren's syndrome and oral lichen planus—a preliminary study on the effects of bovine colostrum-containing oral hygiene products", Clinical Oral Investigations, vol. 6, No. 1, Mar. 2002, pp. 11-20.
G. Duncan et al., "Quality of life, mucositis, and xerostomia from radiotherapy for head and neck cancers: A report from the NCIC CTG HN2 randomized trail of an antimicrobial lozenge to prevent mucositis", Head and Neck, vol. 27, No. 5, May 2005, pp. 421-428.
T. Matsukura et al., "Characterization of Crystalline L-Carnosine Zn (II) Complex (Z-103), a Novel Anti-Gastric Ulcer Agent: Tautomeric change of Imidazole Moiety upon Complexation", Chemical and Pharmaceutical Bulletin, Pharmaceutical Society of Japan, JP, vol. 38, No. 11, Jan. 1990, pp. 3140-3146.
S. Raju et al., "Effect of Sorbitol on Salivary Flow Rate", Journal of Advanced Clinical & Research Insights, vol. 1, No. 1, Jul. 1, 2014, pp. 14-17.
E. J. Baran, "Metal Complexes of Carnosine", Biochemistry (Moscow) vol. 65, No. 7, 2000, pp. 789-797.

* cited by examiner

*Primary Examiner* — Ralph J Gitomer
(74) *Attorney, Agent, or Firm* — Blank Rome LLP

(57) ABSTRACT

The present invention concerns compositions for the increase in the humoral secretion comprising imidazole peptides or extracts containing them, as well as the use of said compositions for the prevention and/or treatment of secretarial dysfunctions of the body mucosa.

24 Claims, 5 Drawing Sheets

METHOD FOR TREATMENT OF HUMORAL SECRETION DYSFUNCTIONS

BACKGROUND

In the medical field, there are known pathologies linked to dysfunctions of the humoral secretions like saliva, tears, vaginal and gastroenteric fluids.

In particular, the saliva is a liquid physiologically produced by the salivary glands of the mouth and has a percentage composition, based on its total weight, of 98% water and for the remaining 2% of electrolytes, enzymes and immunoglobulins.

More in details, the regular secretion of saliva is capable of maintaining the homeostasis of the mouth and, thanks to is peculiar multi-factorial composition, has a lubricant and mechanically cleaning activity, contrasting the bacterial and fungal proliferations, protects the mucosae from the high temperatures of foods and has a buffer activity towards caries, thereby contributing to the mineralization of the early caries lesions.

Today, the reduction in the salivary flux is a known pathology, defined as "xerostomia" meaning literally "dry mouth", whose symptoms depends upon its triggering factors.

Xerostomia is linked to physiological factors such as age (particularly in elderly and post-menopause women), or exogenous factors like pharmaceutical treatments (for example, anti-colynergic, anti-psicotic, anti-staminic or beta-blockers drugs), oncological treatments like radiotherapy and chemotherapy, or systemic autoimmune pathologies (like, for instance, Sjögren syndrome).

Said pathology has several symptoms comprising mouth dryness, thirst, burning, lesions of the oral cavity, swallowing difficulties, hafonia, halitosis and taste alteration.

Moreover, the drastic decrease in the salivar secretion causes a reduction in the defenses of the oral cavity, leading to the development of a pathogenic bacterial flora, which is responsible for the onset of dental lesions, gingivitis, stomatitis, parodontitis, periodontitis, aftae, caries, gingival bleeding, candidosis, mucositis.

It is easy to understand, therefore, that the persistence of such conditions linked to dehydration and lack of protection of the oral cavity, together with the continue accumulation of pathogens, lead to complex clinical frames which may undermine the quality of life of the patients suffering from xerostomia.

Today, the therapeutic options for said pathology are few and with a low efficacy along the time; for example, it is known the use of muscarinic active principles capable of stimulating the salivary secretion from exocrin glands.

It is known the use of drugs having anti-pain activity with the purpose of limiting the effects of dehydration and of the mouth lesions, or of drugs having healing activity aimed at contrasting the proliferation of bacterial and fungal infections of the oral cavity.

However, also said drugs have a temporary effects, reducing the local symptomatology, without intervening on the increase of salivary glands, upstream.

Beyond the secreting dysfunctions of the oral cavity, also the secreting dysfunctions of the vaginal fluids causes important inconveniences to women suffering from them.

Also in this case, the causes triggering said pathologies are multiple and can be referred among those above disclosed as physiological factors linked to age, exogenous factors like pharmaceutical therapies, chemiotherapy and radiotherapy or systemic autoimmune pathologies.

People suffering from said problems experience burning, itch and in some more serious case also bleeding.

The above mentioned factors are also the causes of secretorial tear dysfunctions, which is the cause of ocular dryness and of several serious inconvenience to those suffering from that.

In fact, people who suffer from this disorder are often plagued by burning, itching, difficulty when opening the eyelids on awakening, photophobia and visual fogging; it is easy to understand, therefore, how said inconveniences may affect the quality of life of a person and, if left untreated, can cause permanent damages to eyes.

SUMMARY OF THE INVENTION

The purpose of the present invention is therefore to provide a composition for the increase of the humoral secretions, facilitating the integrity of the mucosa, particularly of the oral mucosa and of its microenvironment.

OBJECT OF THE INVENTION

A first object of the invention is to provide a composition for the increase of the humoral secretions.

Another object of the present invention is to provide a composition for the increase of the oral humoral secretions and, as per alternative aspects of the invention, of the ocular, gastrointestinal, epithelial, genitourinary, respiratory, nasal secretions and secretions of the ear.

According to further object, it is disclosed a method for the prevention and/or treatment of pathologies characterized by the reduction in the humoral secretion comprising the administration of the composition of the invention.

Further objects of the present invention are also disclosed in the following description.

DETAILED DESCRIPTION OF THE INVENTION

According to the first object of the invention, it is disclosed a composition for the increase of the humoral secretion.

In the present description reference is made to a composition for the increase of the humoral secretions, that can be used by a person who suffers from a reduced and/or a lack of lubrication of the oral mucosa.

Alternatively, reference is made to a composition for the increase of the humoral secretions, that can be used by a person who suffers from a reduced and/or a lack of lubrication of the ocular, gastrointestinal, skin, genitourinary, respiratory, nasal mucosa and of the mucosa of the ear.

In particular, the composition comprises imidazole peptides.

For the present purposes, "imidazole peptides" refers to peptides comprising at least one imidazole ring.

These imidazole peptides have at least an histidine residue.

Alternatively, the composition of the invention may comprise animal extracts containing said imidazole peptides.

For instance, animal extracts may be obtained from meat of animals like chicken, turkey, pork, calf, or horse.

Alternatively, the composition of the invention may comprise plant extracts containing said imidazole peptides.

More in particular, said animal or plant extracts may be natural or synthetic.

In a preferred embodiment of the present invention, the imidazole peptides comprise carnosine (N-β-alanylhistidine).

For the present purposes, the term "carnosine" refers the compound N-β-alanyl-histidine (IUPAC name: 2-(3-aminopropanoylamino)-3-(3H-imidazol-4-yl) propanoic acid) and, particularly to both its enantiomeric forms: D-carnosine (N-β-alanyl-D-histidine) and L-carnosine (β-N-alanil-L-histidine), as well as the racemic form, and their mixtures in any proportion (see FIG. 1).

Advantageously, carnosine is present in free form.

According to a further alternative, carnosine may be present in a complexed form with water soluble polymers or fat-soluble polymers.

Alternatively, carnosine may be present in a complexed form with metals.

Metals shall be read as including also metal ions.

For example, carnosine may be present in complexed form with transition metal ions such as $cu^{2+}$, $CO^{2+}$, $Ni^{2+}$, $Cd^{2+}$ and $Zn^{2+}$, $Fe^{2+}$.

Advantageously, carnosine is present in a composition according to the invention in a concentration between about 0.01% and 40% (weight/total weight of the composition).

In a preferred embodiment, carnosine is present in a concentration between about 2% and 20% (weight/total weight of the composition) and, in an even more preferred embodiment, it is present between about 4% and 10% (weight/total weight of the composition).

According to an alternative embodiment of the invention, carnosine may be partially or completely substituted by a substance or a mixture of substances capable of releasing carnosine or obtained by modifications to the molecule of carnosine either on the imidazole ring or to the histidine side chain.

Figure 1:
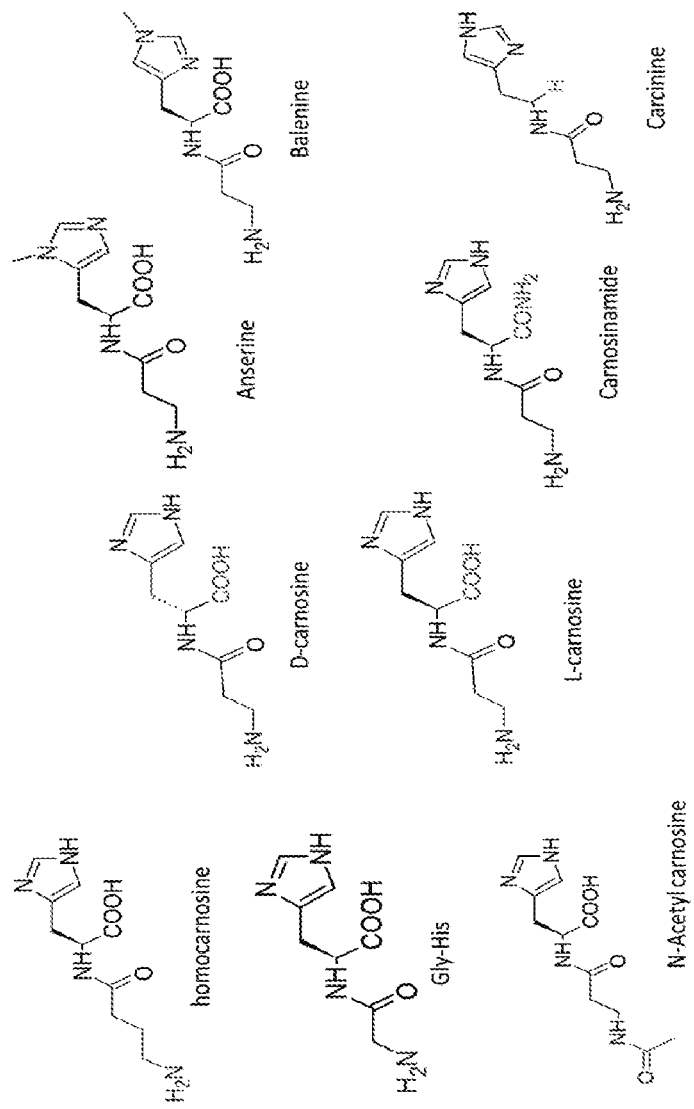
FIG. 1 report the formula of carnosine and of some of its derivatives.

For instance, pharmaceutically acceptable derivatives may be selected in the group comprising anserine (N-β-alanyl-1-methylhistidine), balenine (N-β-alanyl-3-methylhistidine), homocarnosine (N-4-aminobutiryl-histidine), N-acetyl-carnosine, carcinine (β-alanylhistamine), Gly-His, carnosinamide (whose formula are depicted in FIG. 1).

Anserine (N-β-alanyl-1-methylhistidine) is obtained by methylation of nitrogen in position 3 of the imidazole ring of the histidine residue:

Similarly, balenine (N-β-alanyl-3-methylhistidine) is obtained by methylation of the nitrogen in position 1 of the imidazole ring of the histidine residue.

Accordingly, in the whole description of the present invention, carnosine shall also be read as one the derivatives above disclosed and any reference to carnosine shall be read as referring to a carnosine derivative, too.

According to a preferred embodiment of the invention, the composition disclosed comprises organic and/or inorganic acids.

For the present purposes, acids may have either animal or vegetal origin and may be either synthetic or of natural origin.

In a preferred embodiment, the inorganic acid is chloride acid.

According to a preferred embodiment, the organic acid is selected in the group comprising: ascorbic acid, maleic acid, citric acid, lactic acid, acetic acid, tartaric acid, etc.

Mixtures of the above disclosed acids may also be used.

In a preferred embodiment, the acid is a food-grade acids.

In an alternative embodiment, the acid or the mixture of acids may be used in combination with flavonoids.

Advantageously, such a mixture may be found in a plant extract, for instance represented by the vegetal extract of *Hibiscus sabdariffa* L. flos.

The dries calyces of said plant are known to the skilled in the art as "karkadè".

Accordingly, in the following description with the term "karkadè" reference will be made to the dried calyces of *Hibiscus sabdariffa*.

The karkadè comprises different organic acids (malic acid, ibiscic acid, citric acid, tartaric acid, oxalic acid and ascorbic acid, protocatechuic acid), antocyanins, phytosterols and/or flavonoids.

Karkadè has shown to be particularly effective towards *Streptococcus mutans*, a well-known commensal cariogenic of the oral cavity, against which it may act at a minimum inhibitory concentration substantially equal to 2.5 mg/ml.

For the purposes of the present invention, the *Hibiscus sabdariffa* L. flos, i.e. the karkadè, is present in a quantity of between about 0.01% and 40% (weight/total weight of the composition).

In a preferred embodiment, the karkadè is present in a quantity of between about 0.05% and 20% and in an even more preferred embodiment of between about 1% and 10% (weight/total weight of the composition).

According to an embodiment of the invention, the disclosed composition may also comprise an additional vegetal extract or some specific components of a vegetal extract or preparation with the purpose of providing additional properties to the composition.

In particular, the composition of the invention may include *calendula*, *Matricaria chamomilla* (glycolic chamomile extract), *Tamarindus indica* (*Tamarindus indica* xyloglucan), *Calendula arvensis*.

According to a preferred embodiment, the composition of the invention may include colostrum.

"Colostrum" refers to the fluid secreted from the breasts at the end of pregnancy and after childbirth.

In order to ensure the highest hygienic standards and to minimize the risk of zoonoses, colostrum is collected in the Countries at no BSE risk, authorized to produce milk for human consumption and subject to the prophylaxis standards for the safety of food and feeding for animals.

For the present purposes, colostrum may have bovine, equine, caprine origin; preferably, the colostrum is of bovine origin.

In one embodiment, colostrum is present in a concentration between about 0.01% and 60% (weight/total weight of the composition).

Preferably, colostrum is present in a concentration comprised between about 0.1% and 30% and in a more preferred embodiment between about 0.4% and 25% (weight/total weight of the composition).

According to one embodiment of the invention, when colostrum is present in the composition of the invention, it may have the following composition:

| COMPOUND | (% w/total w) |
|---|---|
| carnosine | 4-9% |
| karkadè | 1-6% |
| colostrum | 18-22% |

According to the present invention, the composition disclosed may be formulated for any of the following routes of administration: enteric, inhalation, transdermally, ocular, nasal, vaginal and urethral.

Enteral administration means that the absorption of the composition occurs through the entire oral cavity and the gastrointestinal tract and, therefore, includes the oral, sublingual (or buccal) and rectal administration.

In a preferred embodiment the present composition is administered buccally.

According to a preferred embodiment of the invention, it is disclosed a formulation for the vaginal administration of the composition of the invention.

According to the intended route of administration, the composition of the invention may be formulated as compresses, granules, powder, capsules, pellets, suppositories, tablets, mucoadhesive tablets, dragées, rubbers, cachets, vaginal ovules and suppositories.

Specifically, the generic term "tablet" is to be understood as comprising coated tablets, soluble and dispersible, orodispersible tablets, with modified or extended release, or gastroresistant tablets.

Similarly, the generic term "capsule" is intended to refer to rigid, soft, with modified or extended release, or gastroresistant capsules; with the term "granulate" it is intended also effervescent, coated granulates, granulates with extended-release and gastroresistant granulates.

In addition, the composition of the invention may be formulated as a liquid formulation in a liquid form chosen from the group comprising: solution, suspension, emulsion or spray.

In this case, the generic term "solution" is to be intended as a composition for oral use (for example, syrups and mouthwashes), for topical, rectal or vaginal application, eye drops or eye washes, drops or nasal sprays, solutions for inhalation or for irrigation.

Moreover, the composition may be in a semi-solid form selected from the group comprising: ointment, cream, gel, paste or foam.

For the purposes of preparing a suitable formulation, a composition of the invention may also comprise any one of:
pharmaceutically acceptable carrier/s;
pharmaceutically acceptable excipients chosen from the group comprising: gelling agent, emulsifiers, emollients, buffers, chelating agents, antioxidants, preservatives, flavors, sweeteners, binders, thickeners and viscosity regulators.

A pharmaceutically acceptable carrier or excipient may selected from the group comprising: water, carbomer, polyvinylpyrrolidone, gums including xanthan gum, guar, thara gum, pectin, amylopectin, gelatin, starch, cellulose, derivatives of cellulose selected from the group comprising: hydroxyethylcellulose, carboxymethylcellulose, methylcellulose, hydroxypropylmethylcellulose, hydroxypropylcellulose, glycerine, Mallow mucilage, magnesium stearate, sucralose, sugar, aroma, flavors, a buffer, potassium sorbate, Montanox 80, sodium benzoate, benzalkonium chloride (solution at 50%), chelating agents such as disodium EDTA, plasdone, hyaluronic acid, glycerin, Natrosol 250.

As known to the skilled person in the art the carbomer are cross-linked acrylic polymers with polyalchenylic ethers and commercially known as "Carbopol" (for example, Carbopol 934, 980 and 981).

For the purposes of the present invention, the disclosed composition may comprise carbomer and/or amylopectin, in an overall weight concentration of between about 35% and 45% (weight/total weight of the composition).

It is useful to point out that for the present purposes "mucoadesive compressed" it is intended a solid preparation with adhesion so as to ensure adherence to the oral mucosa and that, by disgregation, there are released their components in a gradual and prolonged way.

The stoichiometric ratio of carbomer and amylopectin allows to have a variable disgregation and release time according to the needs of consumers.

Other excipients for the specific preparation of a mucoadhesive tablet may comprise: D-glucitol, hydroxypropylcellulose, magnesium stearate, sucralose and flavor.

More in detail, D-glucitol, hydroxypropylcellulose, magnesium stearate, sucralose and flavor may be present in the following concentrations:

| Compound | (% w/total w) |
|---|---|
| D-Glucitol | 25-30% |
| hydroxypropyl cellulose | 2-7% |
| magnesium stearate | 0.5-2.5% |
| sucralose | 0.01-0.10% |
| aroma | 0.01-0.20% |

As for one of the objects of the present invention, the disclosed composition may be used in a subject for the treatment and/or prevention of secretory dysfunctions of the mucosae.

More in particular, with "mucosae" it is intended: the oral mucosa, lacrimal, gastrointestinal, rectal, epithelial, genitourinary (especially vaginal), respiratory, nasal and of the ear.

In practice, the present composition can be used for each body area, where there are dysfunctions in the mechanisms of secretion and hydration of the area itself.

More in detail, the composition of the invention can be used for the treatment and/or prevention of xerostomia.

Particularly, the composition can also be used in the treatment and/or prevention of xerostomia caused by oncological diseases.

Alternatively, the composition may be used for the prevention and/or treatment of xerostomia caused by chemotherapy and/or radiotherapy.

In particular, the prevention and/or treatment of xerostomia may be performed with the administration of a pharmaceutically effective amount of a composition of the invention.

Xerostomia may particularly affect the oral secretion.

Similarly, according to the present invention, patients may suffer from a reduction of the oral, ocular, gastroenteric, epithelial, genitourinary, respiratory, nasal secretion and secretion of the ear.

Buccal treatment of xerostomia may also be performed in view of halitosis, aftae, mucositis, lesions cause by braces.

Vaginal treatment may also be performed in view of dryness caused by pharmaceutical treatment, menopause, itch, use of lubricants, etc.

According to a preferred embodiment, a composition of the invention may be administered two to four times per day, preferably four times per day.

In particular, a composition comprising 5.2% (w/w) carnosine and karkadé 2% (w/w) can be administered twice to four times, preferably four times, per day.

For vaginal application, the composition of the invention may be administered twice a day.

As per an additional object of the invention, it is disclosed a method for the prevention and/or treatment of patients suffering from xerostomia.

Alternatively, other dysfunctions of the mucosal secretion may in particular affect the secretion of the ocular, gastroenteric, epithelial, genitourinary, respiratory, nasal mucosa and of the mucosa of the ear.

In particular, the route of administration, the posology, the dosage and the etiology of xerostomia or of any other dysfunctions of the mucosal secretion, may be any one of the administration, posology, dosage and etiology above disclosed.

Example 1

Composition in the Solid Form

A composition is prepared in the form of a mucoadhesive tablet having the following composition:

| Compound | (% w/total w) | mg/cps |
|---|---|---|
| Carnosine | 5.2% | 20.80 |
| Hibiscus sabdariffa L. flos (karkadé) | 2% | 8 |
| Carbomer/amylopectin | 30% | 120 |
| D-glucitol | 58.65% | 234.60 |
| Hydroxypropyl cellulose | 3% | 12 |
| Magnesium stearate | 1% | 4 |
| Sucralose | 0.05% | 0.2 |
| Aroma | 0.10% | 0.4 |

Example 2

Results

As from the following results, the composition of EXAMPLE 1 leads to a significant increase in the salivary flow, leading to an increase of the pH in the oral cavity.

In detail, it has been performed an experimental study based on the selection of five healthy, non-smokers patients aged between 40 and 55 years.

All the five selected subjects showed a marked salivary production of less than 3 g/min which, although within the physiological range, is a value inferior to the average value (4 g/min).

A data collection protocol based on the secretion of saliva was followed at predetermined time intervals over a period of seven days.

Saliva was collected in sterile tubes pre-weighed with ten successive secretions of the duration of ten seconds each after fifty seconds from the end of the previous erogation.

Subsequently, the content of the saliva was determined gravimetrically and the value of the saliva pH measured by an electrode.

The table 1 below shows the days (T0-T6) and the time intervals at which it is carried out the collection of saliva.

TABLE 1

| T0 | T1 | T2 | T3 |
|---|---|---|---|
| Erogation: 11 a.m. | Administration of 4 tablets Erogation: 9 a.m. 11 a.m. 2 p.m. 5 p.m. | Administration of 4 tablets Erogation: 9 a.m. 11 a.m. 2 p.m. 5 p.m. | Administration of 4 tablets Erogation: 9 a.m. 11 a.m. 2 p.m. 5 p.m. |

| T4 | T5 | T6 |
|---|---|---|
| Erogation: 11 a.m. | | Erogation: 11 a.m. |

Based on the data collected according to the protocol of Table 1, it was performed a statistical analysis designed to evaluate the effectiveness of the composition.

FIGS. 2 to 6 show a graphic representation of the results.

Figure 2:
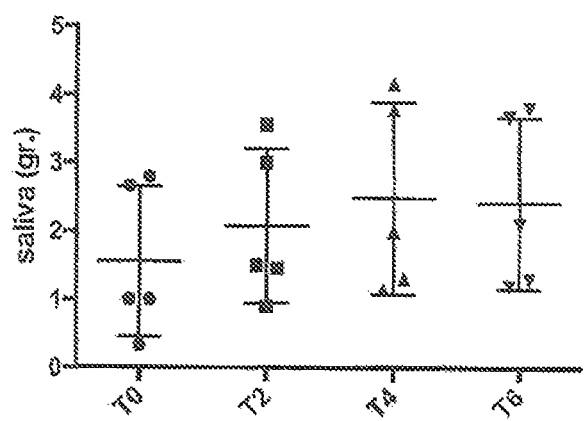
FIG. 2 shows a graph representing the distribution of the data on the production of saliva in five healthy subjects at different times after the treatment with the composition of the invention.

In FIG. 2 it has been reported the distribution of the data relating to the production of saliva in the five healthy subjects at different times, in which it was performed the treatment.

In particular, the one-way analysis of variance (ANOVA) shows a significant difference between the groups ($p<0.05$), while the post-test analysis, performed out using the Dunnet test, a multiple comparison procedure, shows how the increase in salivation compared to T0 ($1.55\pm1.10$ gr/ml) is already significant at T2 ($1:13\pm2.08$; $p<0.05$) to further increase at T4 ($2.49\pm1.40$, $p<0.05$), remaining significant even after cessation of treatment (T6, $2.41\pm1.26$; $p<0.05$).

Next, it was calculated the percentage of variation for each patient with respect to the baseline figure at T0 and observed in FIG. 2.

Figure 3:
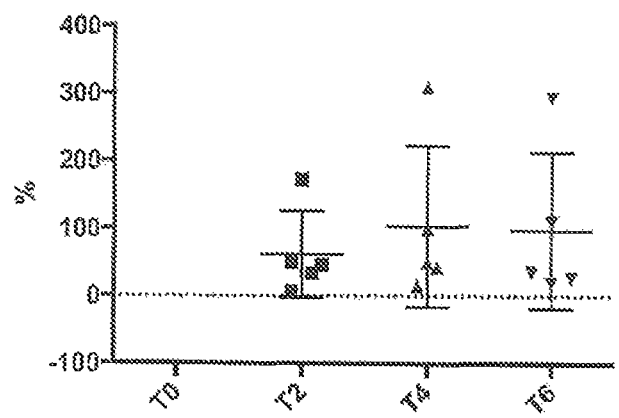
FIG. 3 shows the results of the calculation of the percentage variation for each subject with respect to the basal $T_0$ value.

FIG. 3 shows how the increase in salivation at T2 compared to T0 is $62\pm64\%$ and $104\pm119\%$ to T4.

Finally, it was calculated the increase in saliva production for each individual subject (FIG. 3).

Figure 4:
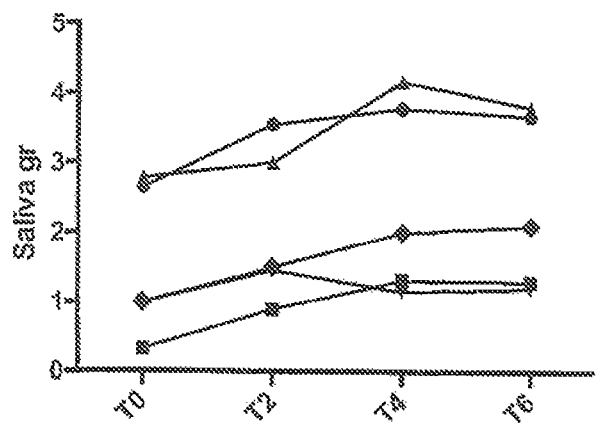
FIG. 4 reports the results for the calculations for the increase in the saliva production for each subject.

From FIG. 4 it appears that all parties benefited from the treatment, showing a progressive time-dependent increase in the salivation, which stops following the treatment.

Figure 5:
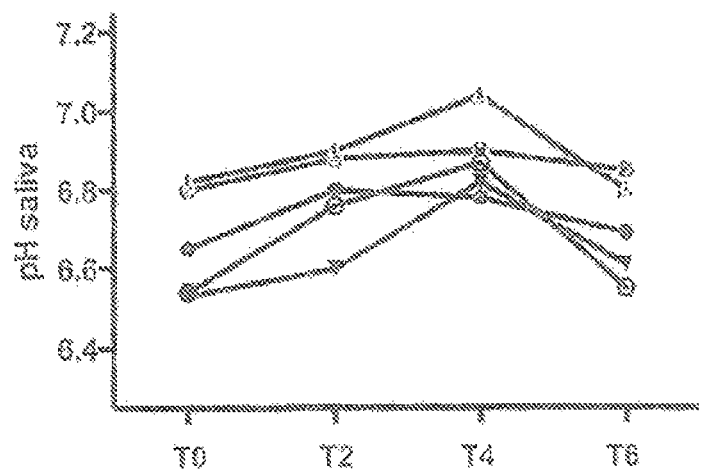
FIG. 5 shows the data calculated for the progressive increase in the pH for each subject.

Furthermore, it has been calculated the progressive increase in pH at different observation times for each individual subject (FIG. 5).

FIG. 5 shows how the increase in the pH value at T2 and T4 compared to the baseline in all patients.

In the light of these data it was performed the analysis of variance to a (ANOVA) showing a significant difference ($p<0.05$) of the pH values recorded at different times during and after the test (FIG. 5).

Figure 6:
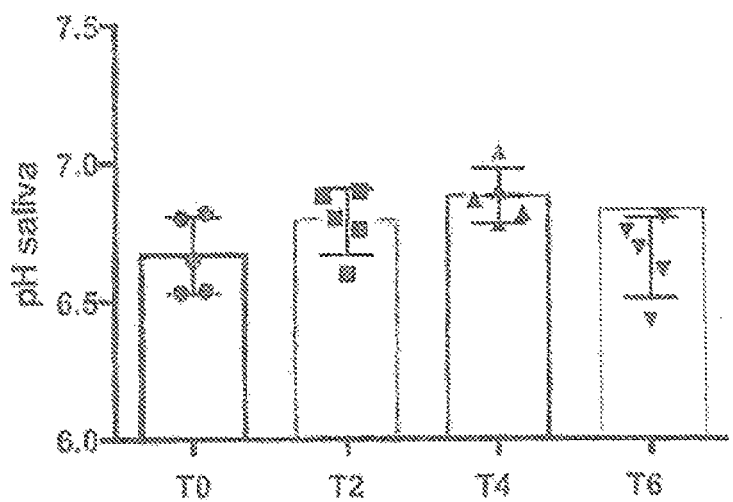
FIG. 6 shows the data for the variance analysis.

In fact, FIG. 6 shows how the average pH recorded at T0 and amounted to $6.67\pm0.14$ increases to $6.79\pm0.12$ at T2 to further increase to $6.88\pm0.10$ at T4.

The statistical analysis showed that the above composition determines, during the treatment, a significant increase in the production of saliva and that it remains substantially constant even after two days following the treatment (T6).

Furthermore, it is stressed that the administration of this composition leads to an increase above 100% after three days of treatment.

Example 3

Composition in the Solid Form

A composition is prepared in the form of a mucoadhesive tablet having the following composition:

| Compound | (% w/total w) |
|---|---|
| Carnosine | 6.5% |
| Karkadè | 3.5% |
| Carbomer/amylopectin | 40% |
| D-glucitol | 23.85% |
| Colostrum | 20% |
| Hydroxypropyl cellulose | 4.5% |
| Magnesium stearate | 1.5% |
| Sucralose | 0.05% |
| Aroma | 0.10% |

Example 4

Compositions in Liquid Form

A composition is prepared in the form of an oral mouthwash.

In case of a formulation for mouthwash, the carrier used is demineralized water.

More in detail, other excipients may include: phosphate buffer, potassium sorbate, Montanox 80, sodium benzoate, benzalkonium chloride (solution at 500), sucralose, flavor for mouthwash, disodium EDTA, glycolic extract of chamomile, plasdone and mucilage of mallow.

By way of example, there are reported the following compositions of mouthwashes:

| Compound | COMPOSITION % (w/total weight) | AN EXAMPLE COMPOSITION % (w/total weight) |
|---|---|---|
| Carnosine | 4-7% | 5.2 |
| Karkadè | 0.05-4% | 2 |
| Phosphate buffer | 40-60% | 50.91 |
| Demineralized water | 30-40% | 37.97 |
| Colostrum | 0.01-0.5% | 0.4 |
| Potassium sorbate | 0.05-0.5% | 0.1 |
| Montanox 80 | 0.05-0.3% | 0.15 |
| Sodium benzoate | 0.05-0.5% | 0.1 |
| Benzalkonium chloride (50% solution) | 0.01-0.1% | 0.05 |
| Sucralose | 0.01-0.1% | 0.05 |
| Aroma for Mouthwash | 0.01-0.1% | 0.02 |
| Disodium EDTA | 0.01-0.05% | 0.05 |
| Glycolic camomile extract | 0.01-5% | 1 |
| Plasdone | 0.01-5% | 1 |
| Mallow mucilage | 0.01-05% | 1 |

Example 5

Composition in the Form of Oral Spray

For the preparation of the composition, demineralized water is used as the carrier.

For said purposes, the excipients may include: potassium sorbate, sodium benzoate, sucralose, polyvinylpirrolidone, hyaluronic acid and vegetable glycerin.

By way of example, there are reported the following oral spray compositions:

| Compound | COMPOSITION % (w/total weight) | AN EXAMPLE COMPOSITION % (w/total weight) |
|---|---|---|
| Carnosine | 4-7 | 5.2 |
| Karkadè | 0.05-4 | 2 |
| Demineralized water | 40-80 | 74.45 |
| Potassium sorbate | 0.05-0.5 | 0.1 |
| Colostrum | 0.01-3 | 1.8 |
| Sodium benzoate | 0.05-05 | 0.1 |
| Sucralose | 0.01-0.1 | 0.05 |
| polyvinylpyrrolidone | 0.05-0.5 | 1 |
| Hyaluronic acid | 0.01-0.5 | 0.3 |
| Vegetable glycerin | 5-20 | 15 |

Example 6

Composition in the Form of a Gel

For the preparation of the composition, water is used as the carrier.

In detail, the excipients may comprise: Natrosol 250, potassium sorbate, sodium benzoate and vegetable glycerin.

In the following exemplified composition, a further vegetable extract is used, such as for instance the *calendula* extract.

By way of example, there are reported the following gel compositions:

| Compound | COMPOSITION % (w/total weight) | AN EXAMPLE COMPOSITION % (w/total weight) |
|---|---|---|
| carnosine | 4-7 | 5.2 |
| karkadè | 0.05-4 | 2.0 |
| natrosol 250 | 0.05-2 | 2.0 |
| potassium sorbate | 0.05-0.5 | 0.1 |
| colostrum | 0.05-5 | 0.4 |
| sodium benzoate | 0.05-0.5 | 0.1 |
| demineralized water | 70-90 | 82.2 |
| vegetable glycerin | 4-8 | 5.0 |
| calendula | 0.05-5 | 3 |

Example 7

Vaginal Composition

The following is an example of a vaginal composition prepared according to the invention.

| Compound | % (w/total weight) |
|---|---|
| Phase 1 | |
| Demineralized water | 92.050 |
| L-carnosine | 0.730 |
| Lactic acid 90% | 0.650 |
| Euxyl K701 | 1 |
| *Tamarindus indica* xyloglucan | 1.5 |
| Xanthan gum EP-USP (Satiaxane UOX911) | 0.9 |
| Phase 2 | |
| Demineralized water | 3 |
| L-carnosine | 0.170 |

Example 8

Results

Experiments have been carried out in order to test the activity of the compositions of the invention for patients suffering from xerostomia.

The tests have been performed with the administration of the composition of EXAMPLE 1 and according to the same protocol.

Figure 7:
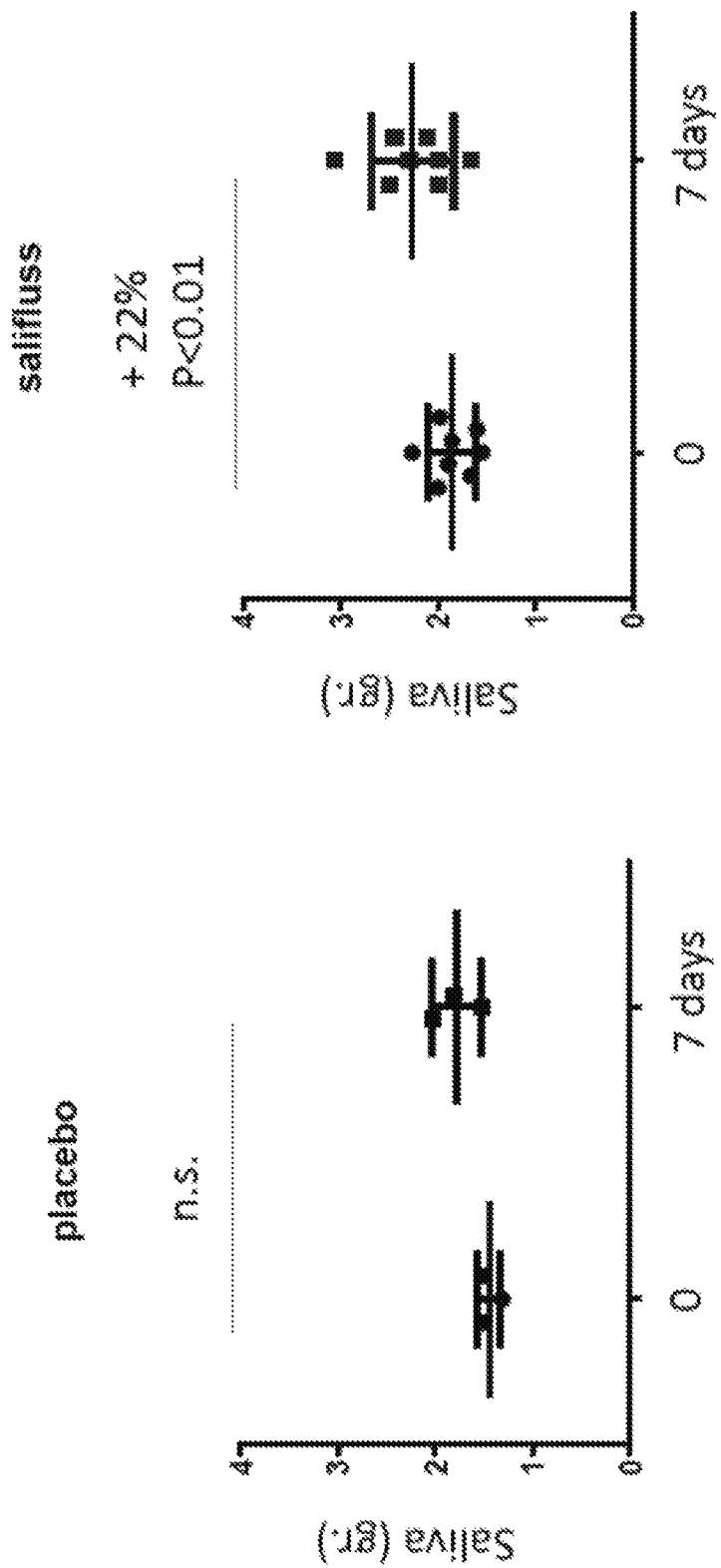
FIG. 7 shows the results of the statistical analysis (paired t-test) for unstimulated saliva secretion test performed on patients suffering from xerostomia treated with a composition of the invention versus placebo.
Figure 8:
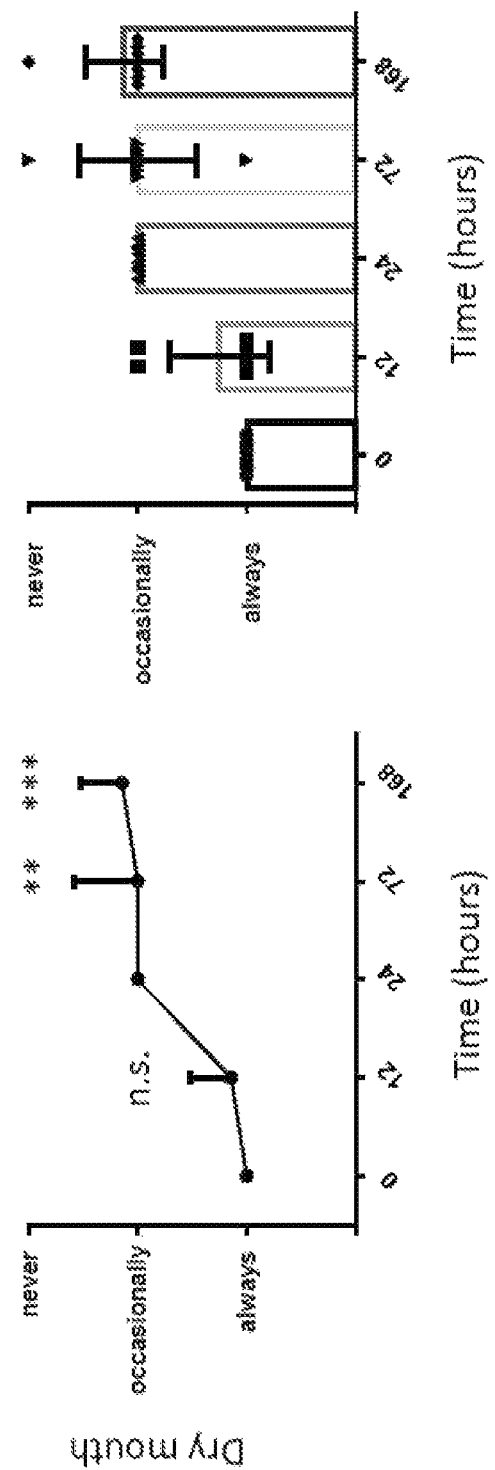
FIG. 8 shows the results of the test performed on patients suffering from xerostomia for testing the dry mouth sensation after administration of a composition of the invention (Statistical analysis: ANOVA one way; Dunnett's multiple comparisons test; comparison of each column with the mean of 0 hour.

The results are reported in FIGS. 7 and 8.

It has been confirmed that the described invention achieves the intended purposes.

Interestingly, when the results are compared to those of Example 2 it can be seen that the dry mouth sensation is improved both in healthy subjects and in subjects suffering from xerostomia.

It is stressed that the special composition the present invention allows the synergic increase of the humoral secretions leading to an increase in salivary flow, promoting the integrity of the oral mucosa and at the same time showing antimicrobial.

Those skilled in the art will be able to make modifications or adaptations to the present invention, without anyhow departing from the scope of the claims set forth below.

The invention claimed is:

1. A method for the prevention and/or treatment of humoral secretion dysfunctions by increasing humoral secretion, comprising the administration of a pharmaceutically effective amount of a composition comprising carnosine or a pharmaceutically acceptable derivative thereof and an acid or a mixture of acids, wherein said acid or mixture of acids comprises an organic acid selected from group comprising one or more of: ascorbic acid, maleic acid, citric acid, lactic acid, acetic acid, and tartaric acid, and wherein said carnosine or pharmaceutically acceptable derivative thereof is present in a quantity between about 0.01-40% weight/total weight of the composition.

2. The method according to claim 1, wherein said humoral secretion dysfunctions are dysfunctions of the mucosae, including oral mucosa, lacrimal, gastrointestinal, rectal, epithelial, genito-urinary, respiratory, nasal mucosa or of the mucosa of the ear.

3. The method according to claim 1, wherein said humoral secretion dysfunction is xerostomia.

4. The method for the prevention and/or treatment of humoral secretion dysfunctions according to claim 1, wherein said humoral secretion dysfunctions are caused by oncologic pathologies.

5. The method for the prevention and/or treatment of dysfunctions according to claim 1, wherein said humoral secretion dysfunctions are caused by chemotherapy and/or radiotherapy.

6. The method for the prevention and/or treatment of dysfunctions according to claim 1, wherein said humoral secretion dysfunctions are related to age or are caused by pharmaceutical treatment or by systemic autoimmune pathologies.

7. The method according to claim 1, wherein said humoral secretion is salivation.

8. The method according to claim 1, wherein said carnosine or a pharmaceutically acceptable derivative thereof is in the free form or it is complexed with metals or metal ions selected from: $Cu^{2+}$, $Co^{2+}$, $Ni^{2+}$, $Cd^{2+}$, and $Fe^{2+}$.

9. The method according to claim 1, wherein said pharmaceutically acceptable derivative is selected from: anserine (N-β-alanyl-1-methylhistidine), balenine (N-β-alanyl-3-methylhistidine), homocarnosine (N-4-aminobutiryl-histidine), N-acetyl-carnosine, carcinine (β-alanylhistamine), Gly-His and carnosinamide.

10. The method according to claim 1, wherein said carnosine or a pharmaceutically acceptable derivative thereof is present in a quantity between about 2-20% (weight/total weight of the composition).

11. The method according to claim 1, wherein said carnosine or a pharmaceutically acceptable derivative thereof is present in a quantity between about 4-10% (weight/total weight of the composition).

12. The method according to claim 1, wherein the composition further comprises one or more polyphenols and/or anthocyanins and/or phytosterols and/or flavonoids.

13. The method according to claim 12, wherein said one or more anthocyanins and/or phytosterols and/or flavonoids are provided in the vegetal extract of *Hibiscus sabdariffa* L. flos.

14. The method according to claim 1, wherein the composition further comprises a vegetal extract or a mixture of vegetal extracts.

15. The method according to claim 14, wherein the vegetal extract is *Hibiscus sabdariffa* L. flos provided in an amount of between about 0.01-40% (weight/total weight of the composition).

16. The method according to claim 14, wherein said vegetal extract is *Hibiscus sabdariffa* L. flos provided in an amount of between about 0.05-20% (weight/total weight of the composition).

17. The method according to claim 14, wherein said vegetal extract is provided in an amount of between about 1-10% (weight/total weight of the composition).

18. The method according to claim 1, wherein the composition further comprises colostrum.

19. The method according to claim 18, wherein said colostrum is provided in a concentration of about 0.01-60% (weight/total weight of the composition).

20. The method according to claim 1, wherein said carnosine may be partially or completely substituted by a substance or a mixture of substances capable of releasing carnosine or obtained by modifications to the molecule of carnosine either on the imidazole ring or to the histidine side chain.

21. The method according to claim 1, in a form selected from: compresses, granules, powder, capsules, pellets, suppositories, tablets, mucoadhesive tablets, dragées, rubbers, cachets, vaginal ovules and suppositories, solution, suspension, emulsion, spray, syrups, mouthwashes, solution for topical application, solution for rectal and vaginal application, eye drops, eye washes, drops and sprays for nasal application, solutions for inhalation and for irrigation, ointments, creams, gel, paste, foam.

22. The method according to claim 1, for enteral application, for inhalation, for transdermal, ocular, nasal, vaginal or ureteral application.

23. The method according to claim 1, wherein the composition further comprises one or more pharmaceutically acceptable carrier and/or excipients selected from: gelling agents, emulsifiers, emollients, buffers, chelating agents, antioxidants, preservatives, flavors, sweeteners, binders, thickeners and viscosity regulators.

24. The method according to claim 23, wherein said pharmaceutically acceptable carrier or excipient is selected from: water, carbomer, polyvinylpyrrolidone, gums including xanthan gum, guar, thara gum, pectin, amylopectin, gelatin, starch, cellulose, derivatives of cellulose selected from: hydroxyethylcellulose, carboxymethylcellulose, methylcellulose, hydroxypropylmethylcellulose, hydroxypropylcellulose, glycerine, mallow mucilage, magnesium stearate, sucralose, sugar, aroma, flavors, a buffer, potassium sorbate, polysorbate 80, sodium benzoate, benzalkonium chloride (solution at 50%), chelating agents such as disodium, ethylenediaminetetraacetic acid, plasdone, hyaluronic acid, glycerin, hydroxyethyl cellulose.

\* \* \* \* \*